(12) United States Patent
Weill et al.

(10) Patent No.: US 8,851,336 B2
(45) Date of Patent: Oct. 7, 2014

(54) DISPOSABLE DEVICE FOR EJECTING A LIQUID OR PASTY PRODUCT

(75) Inventors: David Weill, Begnins (CH); Pierre-Yves Chassot, Thoiry (FR)

(73) Assignee: Primequal S.A., Begnins (CH)

( * ) Notice: Subject to any disclaimer, the term of this patent is extended or adjusted under 35 U.S.C. 154(b) by 556 days.

(21) Appl. No.: 12/529,973

(22) PCT Filed: Feb. 19, 2008

(86) PCT No.: PCT/IB2008/050593
§ 371 (c)(1),
(2), (4) Date: Sep. 4, 2009

(87) PCT Pub. No.: WO2008/107813
PCT Pub. Date: Sep. 12, 2008

(65) Prior Publication Data
US 2010/0105003 A1  Apr. 29, 2010

(30) Foreign Application Priority Data
Mar. 7, 2007 (FR) ...................... 07 01649

(51) Int. Cl.
*A61C 5/04* (2006.01)
*A61M 5/315* (2006.01)
*A61M 5/31* (2006.01)
*A61M 5/24* (2006.01)
*A61M 5/34* (2006.01)

(52) U.S. Cl.
CPC ... *A61M 5/31581* (2013.01); *A61M 2005/2492* (2013.01); *A61M 5/31595* (2013.01); *A61M 2005/341* (2013.01); *A61M 5/24* (2013.01); *A61M 2005/2407* (2013.01); *A61M 5/3129* (2013.01)

USPC .......................................... 222/327; 222/391

(58) Field of Classification Search
CPC .................................................... A61M 5/31581
USPC ........ 222/327, 391; 433/90; 604/224; 401/66
See application file for complete search history.

(56) References Cited

U.S. PATENT DOCUMENTS 1,467,282 A * 9/1923 Bergen ............................ 401/66
3,161,325 A * 12/1964 Hinkel et al. .................... 222/80

(Continued)

FOREIGN PATENT DOCUMENTS

EP  0 276 474 A  8/1988
EP  1 495 777 A  1/2005

(Continued)

OTHER PUBLICATIONS

Examination report issued by Israeli patent office for corresponding Israeli patent application 200762.

(Continued)

*Primary Examiner* — Daniel R Shearer
(74) *Attorney, Agent, or Firm* — Frommer Lawrence & Haug LLP; Ronald R. Santucci

(57) ABSTRACT

Device for ejecting a liquid or pasty product, comprising a body (2) that has a portion (2a) designed to contain the product to be ejected and that has a hole (13) for ejecting the product, a rack (3) that moves in a bore (20) in the body (2) and causes the volume of the portion (2a) designed to contain the product to vary, and a rack (3) movement mechanism comprising a pivoting lever (1) and a pawl (4) for acting on the rack (3), which device is characterized in that the pawl (4) and the lever (1) form a one-piece plastics structure.

20 Claims, 5 Drawing Sheets

(56) References Cited

U.S. PATENT DOCUMENTS

| | | | |
|---|---|---|---|
| 4,099,548 A * | 7/1978 | Sturm et al. | 141/27 |
| 4,472,141 A * | 9/1984 | Dragan | 433/90 |
| 4,710,172 A * | 12/1987 | Jacklich et al. | 604/118 |
| 4,710,178 A * | 12/1987 | Henri et al. | 604/209 |
| 4,779,770 A | 10/1988 | Herold | |
| 4,820,287 A * | 4/1989 | Leonard | 604/209 |
| 5,433,352 A * | 7/1995 | Ronvig | 222/391 |
| 5,570,821 A * | 11/1996 | DeJonge | 222/391 |
| 5,891,106 A * | 4/1999 | Butuzov et al. | 604/209 |
| 6,096,002 A * | 8/2000 | Landau | 604/68 |
| 6,260,737 B1 * | 7/2001 | Gruendeman | 222/391 |
| 7,448,868 B2 | 11/2008 | Delval et al. | |
| 7,571,838 B2 * | 8/2009 | Wolter et al. | 222/391 |
| 2003/0186190 A1 * | 10/2003 | Lokhandwala et al. | 433/89 |
| 2005/0119612 A1 * | 6/2005 | Delval et al. | 604/93.01 |
| 2006/0264838 A1 | 11/2006 | Volckmann et al. | |

FOREIGN PATENT DOCUMENTS

| | | |
|---|---|---|
| FR | 2 535 206 A | 5/1984 |
| GB | 1205052 | 9/1967 |
| JP | 59-131361 | 7/1984 |
| JP | 63-194734 | 1/1988 |
| JP | 2005-521482 | 4/2003 |
| RU | 2031664 C1 | 3/1995 |
| SU | 1591989 A1 | 9/1990 |
| WO | WO 94/12228 A | 6/1994 |
| WO | WO 03/082387 A | 10/2003 |
| WO | WO 2005/007224 A | 1/2005 |
| WO | WO 2005084819 A2 * | 9/2005 |

OTHER PUBLICATIONS

Search report issued in the corresponding Georgian Patent Application No. 11497/01.
Examination report issued by Japanese patent office for corresponding Japanese patent application JP 2009-552305.
Examination Report issued by Australian Patent Office for corresponding Australian application 2008222407 dated Jun. 24, 2012.
Examination Report issued by European Patent Office for corresponding European application 08710086.3 dated Feb. 9, 2010 (in French).
Examination Report issued by European Patent Office for corresponding European application 08710086.3 dated Aug. 20, 2012 (in French).
Examination Report issued by Chinese Patent Office for corresponding Chinese application 2008800074366 dated Apr. 25, 2011(English translation).
Examination Report issued by Chinese Patent Office for corresponding Chinese application 2008800074366 dated Mar. 26, 2012(English translation).

* cited by examiner

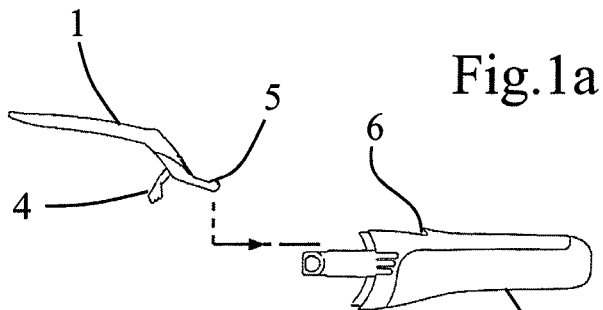
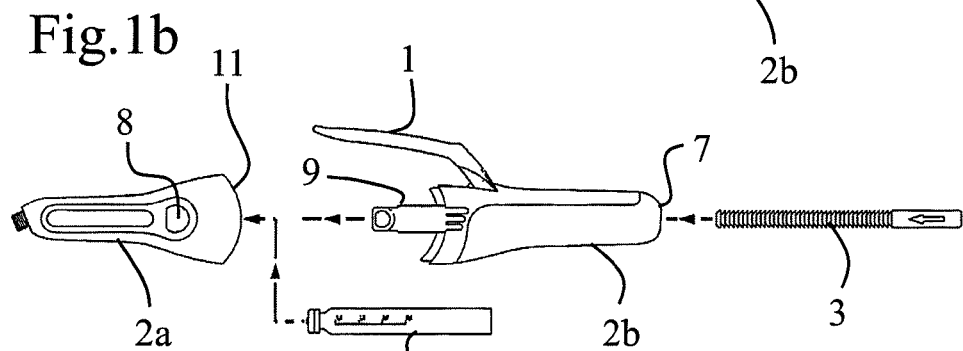
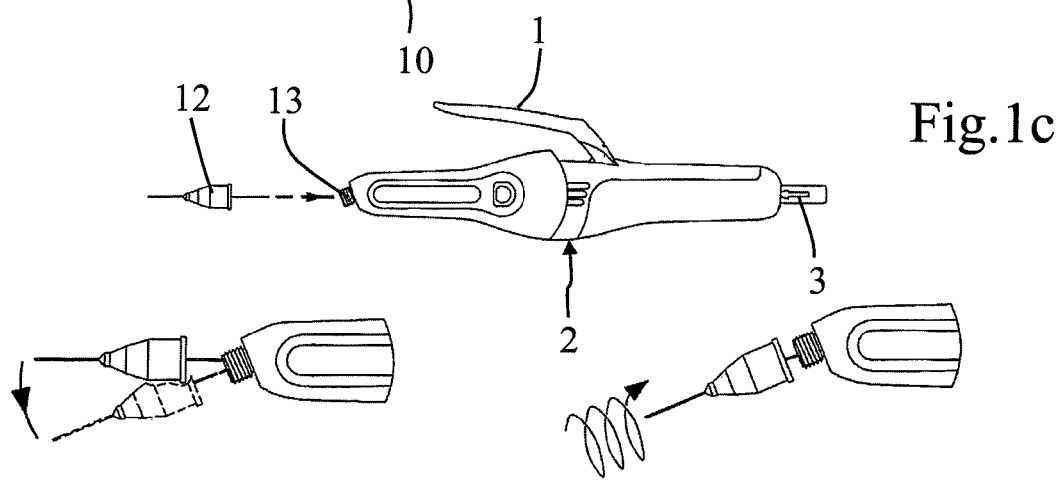
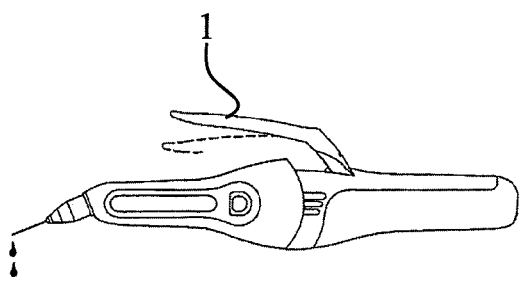

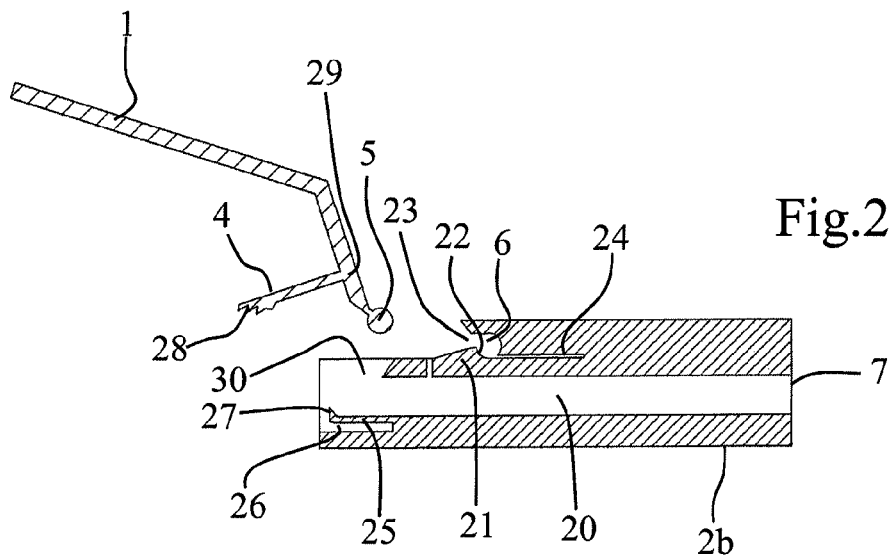
Fig.2
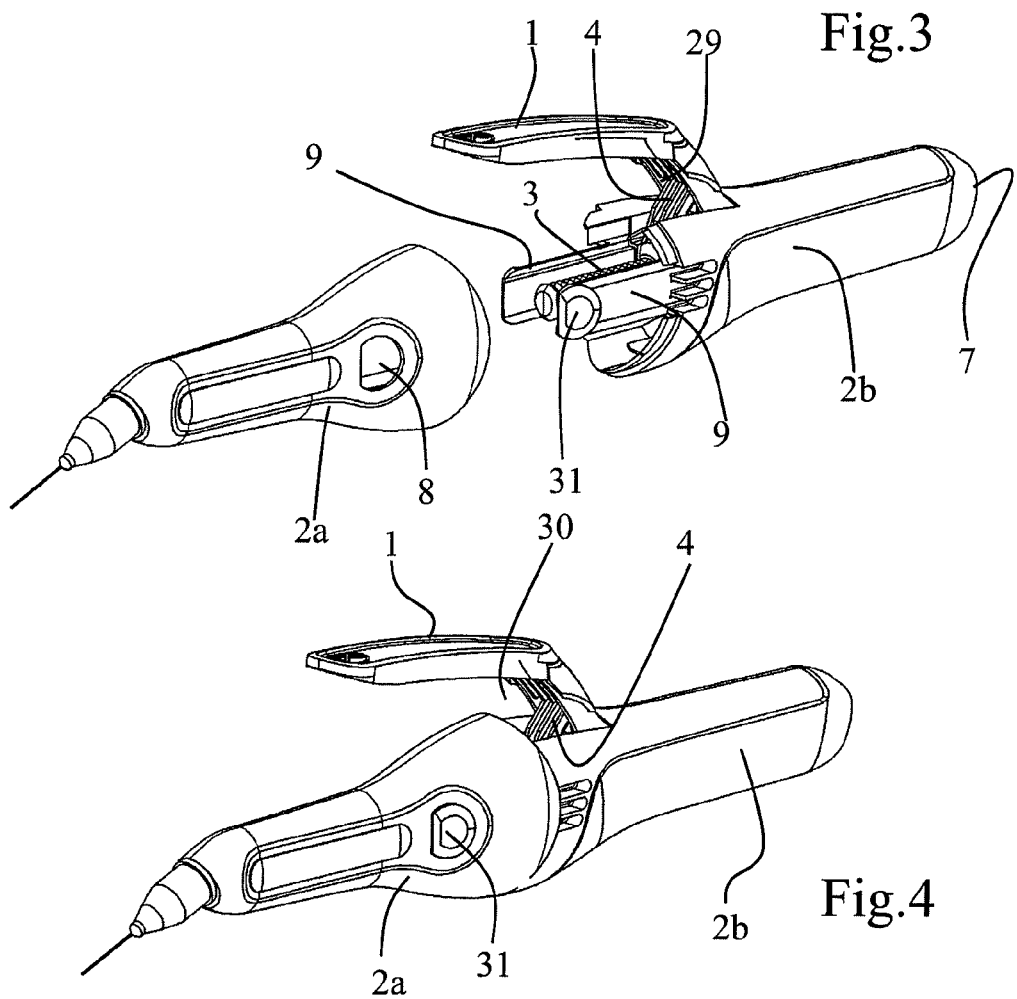
Fig.3
Fig.4

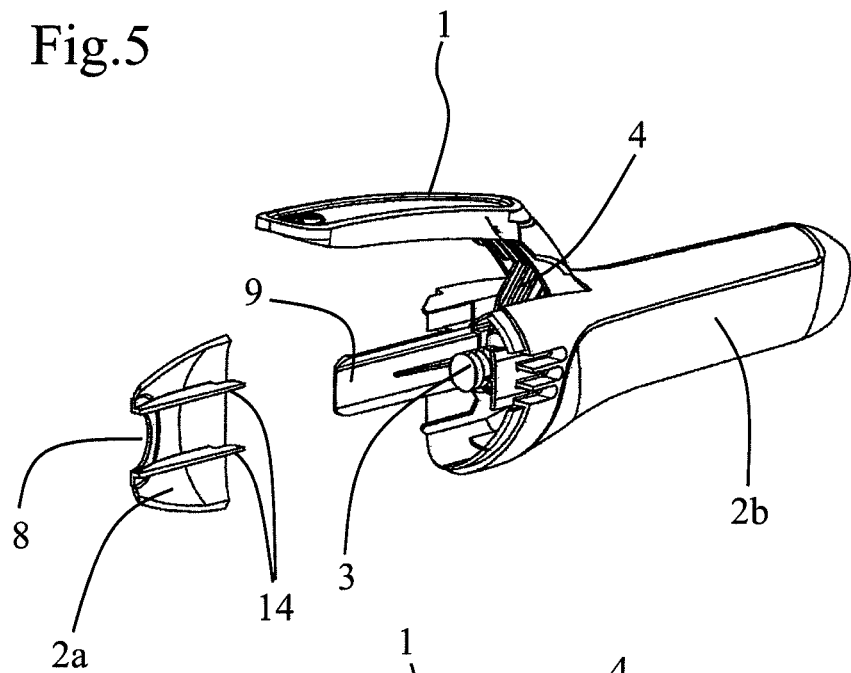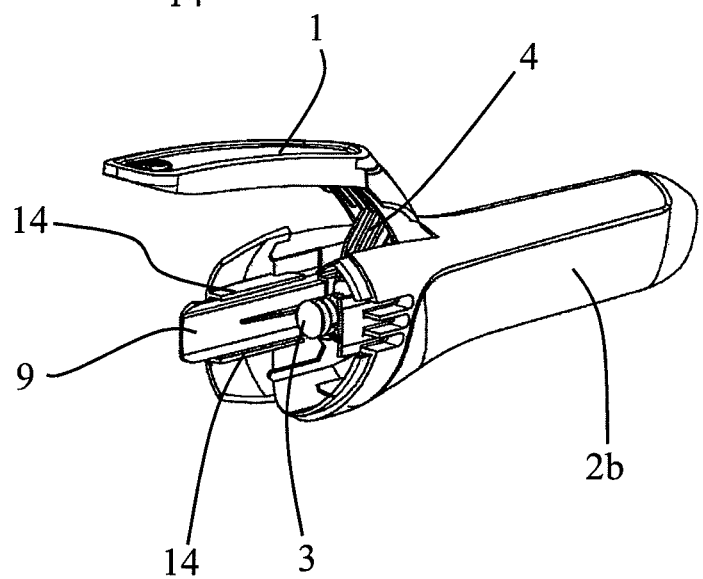

DISPOSABLE DEVICE FOR EJECTING A LIQUID OR PASTY PRODUCT

This application is a 371 of PCT/IB2008/050593 filed on Feb. 19, 2008, published on Sep. 12, 2008 under publication number WO 2008/107813 A1 which claims priority benefits from French patent application Ser. No. 07/01649 filed Mar. 7, 2007, the disclosure of which is incorporated herein by reference.

The invention relates to a device for ejecting a liquid or pasty product, and a method of making and distributing the device.

A dental syringe for intra-ligamentary injection is known from patent application FR 2 535 206. This syringe allows injection by a very fine flexible needle of a product into the ligaments between the jawbone and the tooth. It consists basically of a long body on which a mechanism is mounted for bringing about injection through the movement of a push cylinder, a container holder accommodating a container filled with liquid to be injected, and an end piece comprising the injection needle. In order to solve problems of difficulty of access to the areas where injections must be made, the body of the syringe has an injection head which forms an angle with the axis of the body of the syringe. The needle, which is removable, is fitted to the body before injections are performed and removed afterwards. The injecting mechanism consists basically of a lever hinged to the syringe body and acting on a push cylinder through a pawl hinged to the lever and returned to a position of contact with the teeth of a rack formed on the push cylinder. The cylinder is guided translationally along a bore formed in the syringe body. It also has a longitudinal groove engaging with a screw which is screwed radially with respect to the bore and enters the bore to prevent the cylinder rotating. The mechanism also has a non-return pawl to prevent backward movement of the push cylinder when the action on the lever ends. This non-return pawl is returned to a position of contact with the rack teeth and can be moved out of this position by pressing a button to discontinue the injection pressure and/or to change the injectable product container on which the push cylinder is pushing. There are drawbacks with such a device. First of all, it is complicated and expensive to produce. Secondly, it has many parts and complicated shapes, especially angles and corners in the material. These angles and corners are difficult to access and therefore very difficult to clean and hence difficult to sterilize.

As a partial solution to the above drawbacks, document WO2005/007224 provides an ejection device of a simpler construction which is easily dismantled and cleaned. This device comprises a body, a portion which is designed to contain the product and has a hole for ejecting the product, a toothed push cylinder traveling along a bore inside the body and varying the volume of the portion designed to contain the product, and a mechanism for moving the push cylinder connected to the body, comprising a detachable hinged lever, returned by a return spring, acting on the teeth of the push cylinder through a pawl hinged to the lever and returned to a position of contact with the push cylinder by a spring and a non-return pawl returned to a position of contact with the push cylinder. Despite its great simplicity and the presence of a detachable lever making cleaning easier, this device is still unsatisfactory from the point of view of hygiene and still requires careful cleaning. What is more, the detachable connection of the lever to the body of the device is achieved to the detriment of the performance of the device, because it results in a weaker lever, which undergoes large forces when carrying out an ejection. Last of all, this device, like the previous device, requires an at least partial pre-assembly before distribution, as assembling it would otherwise be too difficult because of the number of parts of the device.

Hence, a general object of the invention is to provide a device for ejecting a liquid or pasty product that alleviates the drawbacks of existing devices.

More specifically, the invention seeks to achieve all or some of the following particular objects.

One object is to provide a device for ejecting a liquid or pasty product offering a maximum degree of hygiene.

A second object is to provide a device for ejecting a liquid or pasty product very efficiently.

A third object is to provide an economic method for making and distributing an ejection device.

The invention achieves the above objects by employing the totally different concept of a disposable ejection device, in the form of a still further simplified and very cheap ejection device.

More precisely, the invention is based on a device for ejecting a liquid or pasty product, comprising a body, having a portion which is designed to contain the product to be ejected and is provided with a hole for ejecting the product, a rack which moves along a bore inside the body and varies the volume of the portion designed to contain the product, and a rack movement mechanism comprising a hinged lever and a pawl for acting on the rack, said device being characterized in that the pawl and the lever form a monolithic structure made of plastic.

For this purpose, the pawl may be approximately perpendicular to the lever and may be connected to the lever at a connection zone having recesses and/or zones of reduced thickness to form a zone of reduced stiffness that is deformable to allow relative elastic movement between the pawl and the lever. The pawl may also have a flexibility suitable for ejection in two steps, an initial step consisting in its deformation without ejection, with increasing pressure on the rack, and a second step consisting in the rack advancing the product being ejected.

The lever may comprise a pivot pin at its end forming a single monolithic structure with the lever and the pawl.

Lastly, the device may comprise a means for locking the connection between the lever and the body.

For this purpose, the body of the ejection device may comprise a seat whose shape corresponds to the shape of the pivot pin in order to house the pivot pin, and at least one leaf spring for snap-engaging the pivot pin of the lever in the seat of the body. This leaf spring may be integrated into the body, on the upper surface of the bore, in such a way that it can deform into this bore to allow the lever to be assembled onto the body and is then no longer able to deform and locks the lever to the body when the rack is present inside the bore.

The leaf spring may have a rounded upper surface which conforms to the pivot pin and positions it correctly in the seat when the rack is inserted.

In a second advantageous form, the ejection device may comprise a leaf spring integrated into the body and fulfilling the function of a non-return pawl. The end of this non-return pawl may be positioned forward of or level with the end of the pawl connected to the lever.

In a third advantageous version, the body of the ejection device may be made up of the assembly of at least one container holder and a rear body, the container holder representing the front portion of the body and the rear body its rear portion, the two portions being connectable by at least two longitudinal leaf springs on one portion positioned in tracks in the other portion. The springs may have at their end a protuberance able to click into openings in the other portion.

In an advantageous variant, the connection between the two portions of the body is locked or virtually locked, thereby locking all of the assembled components for a single use of the device, which is disposable. In another variant, the connection between the two portions of the body is separable to allow the device to be disassembled for cleaning purposes.

In a preferred embodiment of the invention, the device for ejecting a liquid or pasty product is made up of four assembled main portions, a lever which incorporates a pawl, a container holder, a rear body and a rack, at least the lever, the container holder and the rear body being optionally made of an injection-molded plastic.

In one possible variant, at least the container holder is made of a transparent plastic.

The body of the device may have a forward end for accommodating a tool holder with a needle, this forward end having a shape which is inclined relative to the body and has generatrices parallel to the body to enable straight insertion of the needle.

In a final variant, the ejection device includes a skirt in the rear body.

The invention also relates to a method of making an ejection device comprising at least three plastic injection-molding steps for forming three separate portions of the device, a lever incorporating a pawl, a container holder and a rear body. It may include a fourth plastic injection-molding step for forming a rack.

In a variant, the method of making a device for ejecting a liquid or pasty product may include a step of making at least four distinct parts, a lever incorporating a pawl, a container holder, a rear body and a rack, and it may include a method of assembling these four parts comprising the following steps:
 a) inserting the lever onto the rear body, and
 b) inserting the rack into a bore in the rear body and connecting the container holder onto the front of the rear body.

Lastly, the invention relates to a method of distributing a device for ejecting a liquid or pasty product, characterized in that it comprises the step of distributing at least four separate unassembled parts, a lever incorporating a pawl, a container holder, a rear body and a rack.

These and other objects, features and advantages of the present invention are set out in detail in the following description of one particular embodiment presented without implying any limitation with reference to the appended figures, in which:

FIGS. 1a to 1d show schematically different steps in the assembly of an ejection device in one embodiment of the invention;

FIG. 2 is a schematic view in cross section on a longitudinal vertical plane passing approximately through the middle of the device of part of the ejection device in accordance with the embodiment of the invention, showing the connection of the lever to the body;

FIG. 3 is a perspective view of the assembly of the device corresponding to FIG. 1b;

FIG. 4 is a perspective view of the assembled device;

FIG. 5 is a partial perspective view of the assembly of the device corresponding to FIG. 1b;

FIG. 6 is a partial perspective view of the assembled device;

Figure 9:
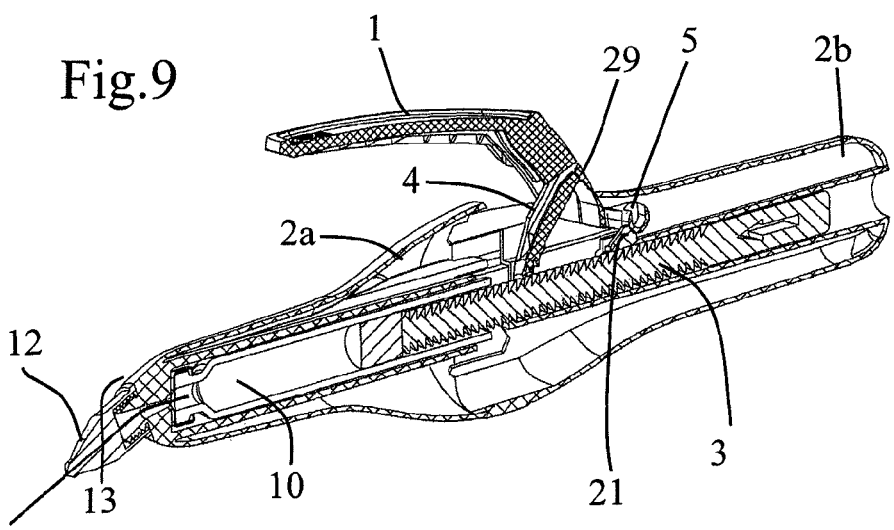
Figure 10:
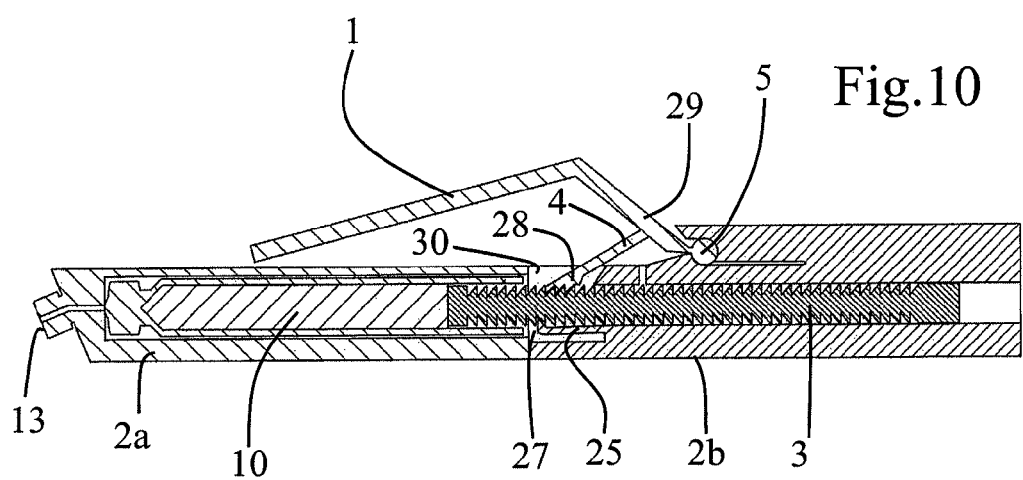

FIG. 9 is a view of the ejection device in the embodiment of the invention in a front perspective view taken on a longitudinal vertical plane passing approximately through the middle of the device; and FIG. 10 shows the operation of the ejection device according to the embodiment of the invention in a schematic sectional view taken on a longitudinal vertical plane passing approximately through the center of the device.

In the preferred embodiment, the ejection device of the invention is based on assembling four separate main parts, shaped in such a way as to allow them to be made from plastic by simple injection molding, and which can be assembled very simply in accordance with the steps illustrated in FIGS. 1a to 1d.

In the first step, shown in FIG. 1a, a lever 1 is assembled onto a rear body 2b. The lever 1 comprises a horizontal upper portion designed to be operated and a lower end in the form of a pivot pin 5 which is positioned in a corresponding seat 6 in the rear body 2b. In addition, a pawl 4 is connected to the lever 1 in a monolithic structure and extends downwards towards the interior of the body 2b.

In a second step illustrated in FIG. 1b, the front portion of the body of the device, that is the container holder 2a, is assembled onto the forward end of the assembly produced in the previous step by means of clips 9 on the rear body 2b engaging in corresponding openings 8 in the container holder 2a, in such a way as to form a complete body 2. Before this operation the cartridge 10 containing the product to be ejected should be positioned in the container holder 2a. In a variant, this product may already have been placed in the container holder beforehand, optionally directly integrated into the container holder, with no intermediate separate cartridge 10. At the same time, a toothed push cylinder 3, referred to hereinafter as the rack 3, is inserted through an opening 7 in the rear of the rear body 2b and positioned in a cylindrical bore provided for this purpose in the central portion of the body 2.

As shown in FIG. 1c, a tool holder 12 with a needle is connected to the end 13 of the container holder 2a and has an orifice for ejecting the product. This connection may advantageously be in the form taught in document WO03/082387. For this purpose the forward shape of the container holder 2a is generally at an angle relative to the body 2 and it has a surface whose generatrices are essentially parallel to the axis of this body 2 in order to allow straight insertion of the needle in this direction before bending it and fixing it in the working position. The ejection device is now ready for use, shown in FIG. 1d by the downward movement of the lever 1 about its pivot pin 5 causing the product contained in the cartridge to be ejected by the pressure of the forward surface of the rack 3. In a variant, the tool holder 12 may be integrated into the container holder 2a.

The geometry and technical functions of the various parts of the device will now be detailed.

FIG. 2 shows more specifically the connection between the lever 1 and the rear body 2b and shows the details of the parts involved in the step illustrated in FIG. 1a. The lever 1 has a cylindrical end 5, forming its pivot pin, which fits into a cylindrical seat 6 of corresponding diameter formed in the upper portion of the rear body 2b of the device. This cylindrical seat 6 comprises in its lower portion a longitudinal leaf spring 21 integrated into the body 2b and cut out 24 from a portion of the upper surface of the central cylindrical bore 20 of the rear body 2b. The pivot pin 5 is initially positioned on two side tracks (not shown) formed in the upper portion of the body 2, and then slid back along these tracks which direct it to the opening 23 of the final seat 6, the dimension of the opening being smaller than the diameter of the pivot pin 5. The spring 21 descends into the bore 20 under the pressure of the pivot pin 5 of the lever 1 to allow it to pass and reach its seat 6 through opening 23. The spring 21 then resumes its natural position owing to its elasticity and fits snugly against a lower portion of the circumference of the pivot pin 5.

The lever 1 is also connected to a pawl 4 approximately perpendicular to the lever in a connection zone 29. This pawl 4 comes to an end 28 comprising one or more teeth for acting on a rack, as will be detailed later. The pawl 4 and the rest of the lever 1 form a monolithic structure produced in a single injection molding step. Their connection zone 29 is such that the pawl 4 is movable elastically relative to the lever 1 by rotating about its connection 29 with the lever. To this end, recesses or zones of reduced thickness are provided within the plastic in the connection zone 29, so as to form a zone of reduced stiffness that is deformable relative to the rest of the lever. These recesses may for example delineate a pivot pin extending across the breadth of the lever in the zone 29, connected to the pawl 4 to represent its axis of rotation.

Finally, the rear body 2b has at least one non-return pawl 25 in the form of a longitudinal leaf spring formed by a recess 26 in the body itself during the injection molding of the body 2b, with an end 27 in the form of a point complementary to the teeth of the rack 3, reaching into the bore 20 to engage with these teeth as will be detailed later.

When the lever is in position in the seat 6 of the body 2b, the container holder 2a is assembled onto the body 2b while a rack 3 is inserted into the longitudinal cylindrical bore 20 of the now assembled body via a rear opening 7, until it meets the cartridge 10 containing the product to be ejected. FIG. 3 shows this step corresponding to that in FIG. 1b, in an intermediate configuration in which the rack 3 is already inserted, while the container holder 2a is being prepared for engagement.

To enable them to be joined together, the rear body 2b has two side arms 9 extending longitudinally forwards to engage with complementary tracks 14, lower and upper, against the side walls on the inside of the container holder 2a, as shown in FIGS. 5 and 6. The ends of these arms 9 have an outward protuberance 31 designed to engage with corresponding openings 8 in the container holder 2a. When the arms 9 are inserted into the tracks 14 of the container holder 2a, the protuberances 31 rub against the inner side walls of the container holder 2a, making the arms 9 bend in elastically towards the middle of the body 2. As soon as the protuberances 31 reach the correspondingly shaped openings 8, they click into them due to the elasticity of the arms 9 which spring back to their initial or normal spacing and their longitudinal and parallel direction. The long shape of the arms 9 kept in place all the way along their length by the lower and upper tracks 14, provides a rigid connection between the two portions 2a and 2b of the body without any disconcerting looseness, thus efficiently transmitting all forces during its use. Any other equivalent mechanical connection between these two portions would be suitable.

Also, the insertion of the rack 3 into the bore 20 of the body 2 causes it to bear against the underside of the insertion spring 21 of the lever 1, thereby preventing any downward movement of this spring 21. Consequently the pivot pin 5 of the lever 1 is locked in the seat 6 of the body 2 and can now no longer escape through the smaller opening 23.

In one advantageous version, the upper portion of the spring 21 forms on the one hand a gentle upward slope guiding the pivot pin 5 of the lever 1 into the opening to facilitate the step of assembling it onto the body 2, as explained earlier, and then has a downward rounded surface 22 corresponding to the curvature of the pivot pin 5 such as to form a lower receiving surface of the seat 6 for the pivot pin 5. Incidentally, if the pivot pin 5 of the lever 1 is not positioned snugly in its seat 6 in the initial assembly step depicted in FIG. 1a, but remains for example stuck in an intermediate zone pressing against the leaf spring 21, such that the latter is bent down, the insertion of the rack 3 into the bore 20 will push the spring 21 upwards, which will finally cause the pivot pin 5 to slide away down its slope 22 to the final position of this pivot pin 5, in which it occupies the whole of the space 6, leaving the leaf spring 21 in its horizontal final position. Inserting the rack 3 thus also has an additional function of setting the lever 1 in its final position, thereby ensuring its correct positioning, before locking it in this position.

In an advantageous embodiment of the device, the cartridge inserted into the container holder 2a approaches the arms 9 in the region of the openings 8 in such a way that the reverse movement of the rear body 2b, which would require deforming the arms 9 again by squeezing the protuberances 31 to release them from the openings 8 while simultaneously pulling the body 2b backwards, is made difficult, if not impossible. This geometry thus makes it difficult for the protuberances 31 to escape and locks or virtually locks the assembled body 2, which in turn locks the rack 3 in the central cylindrical bore 20, which in turn locks the lever 1, as explained above. The device as assembled is therefore impossible or very difficult to dismantle and ensures a reliable and highly functional positioning of the various parts.

FIGS. 6 to 9 are different views of the resulting assembled device.

Figure 7:
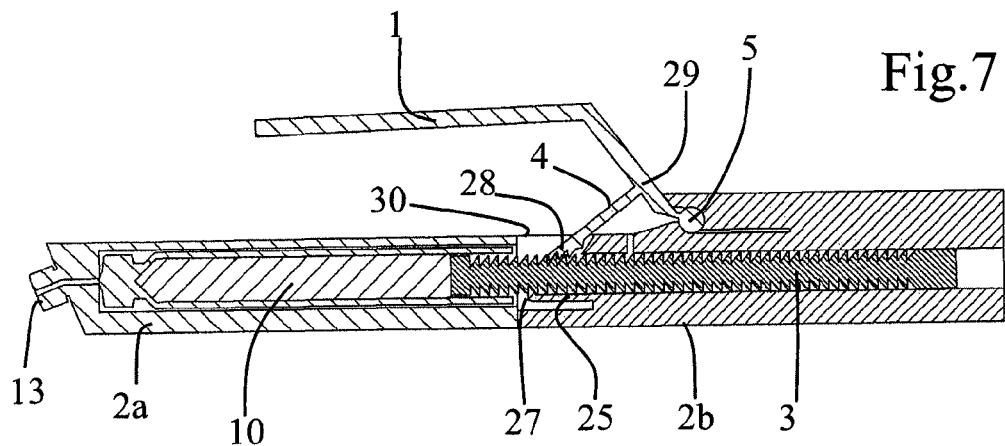
FIG. 7 is a schematic view in cross section on a longitudinal vertical plane passing approximately through the middle of the assembled ejection device.
Figure 8:
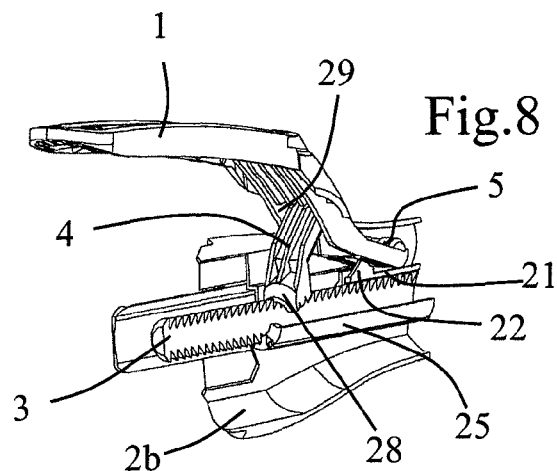
FIG. 8 is a partial perspective rear view of part of the ejection device in the embodiment of the invention.

The toothed end 28 of the pawl 4 of the ejection device, which is shown more clearly in FIGS. 7, 8 and 9, enters an upper opening 30 in the body 2 to approach the teeth of the rack 3, and the end portion 27 of the non-return pawl 25 sits behind one of the teeth of the rack. Insertion of the rack 3 into the bore 20 is accompanied by an audible click when the end 27 of the non-return pawl 25 takes its position between two teeth of the rack. As this end 27 of the non-return pawl 25 occupies a position slightly forward of that of the end 28 of the pawl 4, this audible click occurs when the rack is far enough forward to be able to actuated by the lever 1 and this click tells the user that the rack is far enough forward.

FIG. 10 illustrates the operation of the ejection device. The lever 1 is pressed down against the container holder 2a by rotation about the pivot pin 5, causing an elastic deformation of the pawl 4 (which is pressing against the rack 3) around its connection zone 29 to the lever, thanks to the property of flexibility of the material used and the geometry of the design particularly at the connection 29 between the pawl 4 and the lever 1. This movement of the pawl 4 allows its toothed end 28, engaged with some of the teeth of the rack 3, to push the rack forwards inside the bore 20. In the proposed embodiment, the end 28 of the pawl 4 is rounded to fit the upper cylindrical shape of the rack 3 and three rows of teeth, to engage at the same time with three teeth of the rack 3 and ensure good engagement between these two parts 3, 4.

When the lever is released, the pawl 4 exerts an elastic return force toward its initial position and pushes the lever 1 to its initial raised position. While this is happening the non-return pawl 25 prevents the rack moving backwards. For this purpose its end 27 and the shape of the teeth of the rack have a slope that enables them to slide in the forward direction of the rack, causing a downward deformation of the pawl 25 until the rack tooth escapes from the latter, which then causes the non-return pawl to spring back into the next tooth. This is accompanied by an audible click, confirming to the user that the rack has moved forward. However, the forward surface of the end 27 of the non-return pawl 25 is essentially vertical and engages with a corresponding vertical surface on the teeth of the rack, preventing any rearward movement of the rack. The forward movement of the rack 3 is used to drive a plunger bearing against the volume 10 containing the contents to be ejected.

In one advantageous embodiment of the device, the lever 1 and the pawl 4 are made from injection-molded plastic. Thus, when the lever is actuated, the pawl 4 initially deforms elastically and as it does so exerts greater and greater force on the rack until the latter eventually advances. This two-step behavior allows the effect of a greater or lesser pressure on the lever to be attenuated and results in a relatively constant and gentle ejection of the product, thus improving the well-being of the patient in the case of a syringe. Any excessive pressure on the lever will be partly absorbed by the deformation of the parts of the device.

As explained before, a quick and inexpensive method of making the ejection device is to make the four different essential components of the device—the lever 1, the container holder 2a, the rear body 2b and the rack 3—separately as plastic injection moldings. The material used may be polyamide, polypropylene, ABS or any other plastic. A recyclable plastic will be very suitable for the device, which can be thrown away after use. A transparent plastic may also be used with advantage, especially for the container holder 2a, to enable the user to see how much product to be ejected is left. One final step in the manufacturing method then relates to the method of assembling these components. However, to simplify the transport and distribution of the device, there are advantages in distributing it unassembled, for assembly on site immediately prior to use. This is feasible because of the ease of assembly of the components, as described with reference to FIGS. 1a to 1d. It also means that the end user can choose which product to inject.

In a variant, the aforementioned components may be made differently and in other materials. The rack 3 may for example be made of stainless steel.

A second embodiment of the device according to the invention, though not shown, could be produced on the basis of FIG. 7 of document WO 2005/007224, which differs from the abovementioned embodiment in that the bore 20 has a shoulder to receive a skirt made for example of polytetrafluoroethylene or another plastic material such as a polyetheretherketone (PEEK).

An ejection device of this kind can be used in the medical field for injecting products such as anesthetics into hard tissues, or for depositing adhesives, resins or amalgams. For example, an implementation in an anesthetizing syringe in the dental field is very useful. It can also be used in the paramedical field for depositing predetermined amounts of collagen. Other uses are in micromechanics and jewelry for making adhesive bonds or microwelds or for depositing products.

Lastly, the invention achieves the desired objects and has the following advantages:
the presence of a lever locked securely in place ensures efficient ejection;
the device is based on a simple structure made of few parts, with no separate and independent pivot pin or spring; the parts can easily be produced at low cost by methods compatible with the use of recyclable materials: the manufacturing method is therefore economical and compatible with the disposable device concept, which eliminates cleaning problems; and
the breakdown of the device into a small number of easy-to-assemble parts makes it easy to distribute and easy to assemble at any time even at the moment when an injection is needed.

The device according to the present invention has been conceived on the basis of the concept of a disposable device. However, its non-disposable use, employing the cleaning methods of the prior art, would not be outside of the scope of the invention, because the simplicity of the device and the possibility of making it in multiple separable parts, for example by modifying the connection between the bodies 2a and 2b to facilitate the escape of the arms 9, enables it to be implemented with advantage in a form that can be disassembled for cleaning, simplified by the simplification of the structure of the device.

In addition, the preferred embodiment has been described above. Other embodiments of the invention are possible, using only some of the highly simplified parts of the device, including the lever 1-pawl 4 unit, the device for assembling the lever onto the body 2, the body made up of two main parts 2a, 2b, the non-return pawl 25, etc., which would already make it possible to produce an improved, simplified and less expensive ejection device.

The invention claimed is:

1. A device for ejecting a liquid or pasty product, comprising
a body, having a portion which is designed to contain the product to be ejected and is provided with a hole for ejecting the product,
a rack which moves along a bore inside the body and varies the volume of the portion designed to contain the product, and
a rack movement mechanism comprising
a lever having a pivot pin rotatable about an axis on the body; and
a pawl for acting on the rack,
wherein the pawl and the lever form a monolithic structure made of plastic
a leaf spring forming a portion of the axis and deformable to receive the pivot pin,
wherein the rack when inserted in the bore prevents deformation of the leaf spring to lock the pivot pin in the axis.

2. The device for ejecting a liquid or pasty product as claimed in claim 1, wherein the pawl is approximately perpendicular to the lever.

3. The device for ejecting a liquid or pasty product as claimed in claim 2, wherein the pawl has a flexibility suitable for ejection in two steps, an initial step consisting in its deformation without ejection, with increasing pressure on the rack, and a second step consisting in the rack advancing and the product being ejected.

4. The device for ejecting a liquid or pasty product as claimed in claim 2, wherein the lever comprises a pivot pin at its end forming a single monolithic structure with the lever and the pawl.

5. The device for ejecting a liquid or pasty product as claimed in claim 1, wherein the leaf spring has a rounded upper surface which conforms to the pivot pin and positions the pivot pin correctly in the axis when the rack is inserted.

6. The device for ejecting a liquid or pasty product as claimed in claim 1, wherein the leaf spring is integrated into the body and fulfilling the function of a non-return pawl.

7. The device for ejecting a liquid or pasty product as claimed in claim 6, wherein the end of the non-return pawl is positioned forward of or level with the end of the pawl connected to the lever.

8. The device for ejecting a liquid or pasty product as claimed in claim 1, wherein the body is made up of the assembly of at least one container holder and a rear body.

9. The device for ejecting a liquid or pasty product as claimed in claim 8, wherein the container holder represents the front portion of the body and the rear body the rear portion, the two portions being connected by at least two longitudinal leaf springs on one portion positioned in tracks in the other portion.

10. The device for ejecting a liquid or pasty product as claimed in claim 9, wherein the springs have at their end a protuberance able to click into openings in the other portion.

11. The device for ejecting a liquid or pasty product as claimed in claim 10, wherein the connection between the two portions of the body is locked or virtually locked, thereby locking all of the assembled components for a single use of the device, which is disposable.

12. The device for ejecting a liquid or pasty product as claimed in claim 8, wherein the connection between the two portions of the body is separable to allow the device to be disassembled for cleaning purposes.

13. The device for ejecting a liquid or pasty product as claimed in claim 1, wherein it is made up of four assembled main portions, a lever which incorporates a pawl, a container holder, a rear body and a rack.

14. The device for ejecting a liquid or pasty product as claimed in claim 13, wherein at least the lever, the container holder and the rear body are made of an injection-molded plastic.

15. The device for ejecting a liquid or pasty product as claimed in claim 8 wherein at least the container holder is made of a transparent plastic.

16. The device for ejecting a liquid or pasty product as claimed in claim 15, wherein the body has a forward end for accommodating a tool holder with a needle, this forward end having a shape which is inclined relative to the body and has generatrices parallel to the body to enable straight insertion of the needle.

17. The ejection device as claimed in claim 1, wherein it includes a skirt in the rear body.

18. A method of making a device for ejecting a liquid or pasty product, wherein it includes a step of making at least three parts, a lever incorporating a pawl and a pivot pin, a body having a leaf spring, and a rack the method comprising:
    inserting the pivot pin into an axis on the body, a leaf swing of the body deforming to receive the pivot pin,
    inserting the rack into a bore in the body,
    wherein the rack inserted in the bore prevents deformation of the leaf spring to lock the pivot pin in the axis.

19. The method of making an ejection device as claimed in claim 18, wherein it comprises at least three steps of injection molding a plastic to form three separate portions of the device, a lever incorporating a pawl, and a body.

20. The method of making a device for ejecting a liquid or pasty product as claimed in claim 19, wherein it comprises a fourth step of injection molding a plastic to form a rack.

* * * * *